United States Patent
Kim et al.

(10) Patent No.: US 10,100,160 B2
(45) Date of Patent: *Oct. 16, 2018

(54) SURFACE CROSS-LINKED SUPER ABSORBENT RESIN AND METHOD FOR PREPARING SAME

(71) Applicant: LG Chem, Ltd., Seoul (KR)

(72) Inventors: Young-Sam Kim, Daejeon (KR); Yeon-Woo Hong, Daejeon (KR); Dong-Jo Ryu, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/318,761

(22) PCT Filed: Dec. 14, 2015

(86) PCT No.: PCT/KR2015/013686
§ 371 (c)(1),
(2) Date: Dec. 14, 2016

(87) PCT Pub. No.: WO2016/099102
PCT Pub. Date: Jun. 23, 2016

(65) Prior Publication Data
US 2017/0114192 A1    Apr. 27, 2017

(30) Foreign Application Priority Data
Dec. 18, 2014 (KR) .................. 10-2014-0183227

(51) Int. Cl.
| | | |
|---|---|---|
| *C08F 20/10* | (2006.01) | |
| *C08J 3/24* | (2006.01) | |
| *C08F 2/10* | (2006.01) | |
| *C08J 3/075* | (2006.01) | |
| *C08F 220/28* | (2006.01) | |
| *A61L 15/60* | (2006.01) | |
| *C08F 299/04* | (2006.01) | |
| *C08F 120/06* | (2006.01) | |
| *C08F 2/48* | (2006.01) | |
| *C08F 6/00* | (2006.01) | |

(52) U.S. Cl.
CPC .............. *C08J 3/245* (2013.01); *A61L 15/60* (2013.01); *C08F 2/10* (2013.01); *C08F 2/48* (2013.01); *C08F 6/008* (2013.01); *C08F 20/10* (2013.01); *C08F 120/06* (2013.01); *C08F 220/28* (2013.01); *C08F 299/0464* (2013.01); *C08J 3/075* (2013.01); *C08F 2220/286* (2013.01); *C08J 2333/02* (2013.01)

(58) Field of Classification Search
CPC ... C08J 3/245; C08F 220/28; C08F 2220/286; B01J 20/265; B01J 20/3085; A61L 15/24
See application file for complete search history.

(56) References Cited

U.S. PATENT DOCUMENTS

| | | |
|---|---|---|
| 4,043,952 A | 8/1977 | Ganslaw et al. |
| 4,808,637 A | 2/1989 | Boardman et al. |
| 6,300,275 B1 | 10/2001 | Weir |
| 8,647,317 B2 | 2/2014 | Tian et al. |
| 2004/0157734 A1 | 8/2004 | Mertens et al. |
| 2004/0214946 A1 | 10/2004 | Smith et al. |
| 2005/0020780 A1 | 1/2005 | Inger et al. |
| 2005/0209352 A1 | 9/2005 | Dairoku et al. |
| 2005/0245393 A1 | 11/2005 | Herfert et al. |
| 2007/0232760 A1 | 10/2007 | Fujimaru et al. |
| 2008/0021130 A1* | 1/2008 | McIntosh et al. ...... C08L 51/06 523/111 |
| 2009/0227741 A1 | 9/2009 | Walden et al. |
| 2009/0234314 A1 | 9/2009 | Nakamura et al. |
| 2013/0175473 A1 | 7/2013 | Wada et al. |
| 2014/0058048 A1* | 2/2014 | Won et al. .............. B01J 20/267 525/384 |
| 2015/0197587 A1 | 7/2015 | Lee et al. |
| 2015/0360204 A1 | 12/2015 | Tachi et al. |
| 2017/0095792 A1* | 4/2017 | Kim et al. ............. B01J 20/265 |
| 2017/0144130 A1* | 5/2017 | Kim et al. ............. B01J 20/265 |

FOREIGN PATENT DOCUMENTS

| | | |
|---|---|---|
| CN | 1520425 A | 8/2004 |
| CN | 101045773 A | 10/2007 |
| CN | 103665411 A | 3/2014 |
| CN | 104619749 A | 5/2015 |
| EP | 0574248 A2 | 12/1993 |
| EP | 1736508 A1 | 12/2006 |
| JP | H05339381 A | 12/1993 |
| JP | H06313042 A | 11/1994 |
| JP | H06313043 A | 11/1994 |
| JP | H06313044 A | 11/1994 |
| JP | H08143782 A | 6/1996 |
| JP | 2008106218 A | 5/2008 |
| JP | 5410018 B2 | 2/2014 |
| KR | 20070004669 A | 1/2007 |
| KR | 100873455 B1 | 12/2008 |
| KR | 20090015070 A | 2/2009 |
| KR | 101290740 B1 | 7/2013 |
| KR | 20130097771 A | 9/2013 |
| WO | 9848857 A1 | 11/1998 |

(Continued)

OTHER PUBLICATIONS

Third Party Observation for PCT/KR2015/013686 dated Apr. 18, 2017.

(Continued)

*Primary Examiner* — Nathan M Nutter
(74) *Attorney, Agent, or Firm* — Lerner, David, Littenberg, Krumholz & Mentlik, LLP (57) ABSTRACT

Disclosed herein is a superabsorbent polymer with a surface crosslinked with a water-soluble polyvalent cationic salt, a polycarbonic acid-based copolymer, and a surface crosslinking agent wherein an improvement is brought about in physical properties, with the concomitant reduction of process time and cost. Also, a method is provided for preparing the surface-crosslinked superabsorbent polymer.

22 Claims, 4 Drawing Sheets

(56) References Cited

FOREIGN PATENT DOCUMENTS

WO     2014077516 A1    5/2014
WO     2014119553 A1    8/2014

OTHER PUBLICATIONS

Third Party Observation for PCT/KR2015/013686 dated Apr. 21, 2017.
International Search Report from PCT/KR2015/013686, dated Apr. 4, 2016.
Extended European Search Report for Application No. EP15870269.6 dated Nov. 27, 2017.

* cited by examiner

SURFACE CROSS-LINKED SUPER ABSORBENT RESIN AND METHOD FOR PREPARING SAME

CROSS REFERENCE TO RELATED APPLICATIONS

The present application is a national phase entry under 35 U.S.C. § 371 of International Application No. PCT/KR2015/013686 filed Dec. 14, 2015, which claims priority from Korean Patent Application No. 10-2014-0183227, filed on Dec. 18, 2014, which are incorporated by reference herein.

TECHNICAL FIELD

The present disclosure relates to a surface-crosslinked superabsorbent polymer, and a method for preparing the same. More particularly, the present disclosure relates to a superabsorbent polymer with a surface crosslinked with a water-soluble polyvalent cationic salt, polycarbonic acid-based copolymer, and a surface crosslinking agent, wherein an improvement is brought about in physical properties, with the concomitant effective reduction of process time and cost. Also, the present invention is concerned with a method for preparing the surface-crosslinked superabsorbent polymer.

BACKGROUND ART

Superabsorbent polymers (SAPs) are synthetic polymer materials having a capacity for absorbing 500 to 1000 times their own weight in moisture. Although developed for practical use in sanitary items such as disposable diapers for children, sanitary pads, etc., SAPs now find additional applications in a variety of fields including raw materials in soil conditioners for horticulture, water stopping agents for civil engineering and construction applications, sheets for raising seedlings, freshness preservatives for food distribution, goods for fomentation, and the like. In the synthesis of SAPs, water plays various roles, for example, as a polymerization medium, and to facilitate the dispersion of a cross-linking agent upon surface cross-linking. When absorbing water, however, SAPs increase in stickiness on the resin surface, and their particles undergo irreversible agglomeration. Because this viscosity increase and agglomeration brings about poor processability, such as a load increase, in the preparation and applied processes, the use of silica and organic solvents has been adapted to avoid the problem, but causes the SAPs to decrease in physical properties and productivity and thus to increase in production cost. Particularly, permeability, which is one of the main properties of SAPs for use in pulpless diapers, is degraded as the core-shell structure of SAPs is destroyed during the manufacture of the diapers. To prevent the degradation of such properties a novel approach to the surface crosslinking of SAPs is presented.

Disclosure

Technical Problem

Leading to the present disclosure, intensive and thorough research into SAPs resulted in the finding that SAPs, when modified on their surface with a water-soluble polyvalent cationic salt and a polycarbonic acid-based copolymer, improve in physical properties including permeability, compared to conventional SAPs, even though neither silica nor an organic solvent is employed, whereby effective reduction can be brought about in process time and cost. It is therefore an object of the present disclosure to provide a superabsorbent polymer that is improved in processibility to decrease in a load and to readily control particle sizes and physical properties and wherein the property degradation attributed to the breakdown of the resin in applied processing can be minimized, and a method for preparing the same.

Technical Solution

In order to accomplish the above object, an aspect of the present disclosure provides a surface-crosslinked superabsorbent polymer in which a base resin is treated with a water-soluble polyvalent cationic salt, a polycarbonic acid-based copolymer, and a surface crosslinking agent.

In accordance with another aspect thereof, the present disclosure addresses a method for preparing a surface-crosslinked superabsorbent polymer, comprising:

a) providing a superabsorbent base resin;

b) pre-treating the superabsorbent base resin of step a) by mixing a water-soluble polyvalent cationic salt in an amount of 0.001 to 5.0 parts by weight, based on 100 parts by weight of the superabsorbent base resin provided in step a); and c) subjecting the pre-treated superabsorbent base resin of step b) to surface crosslinking with a mixture solution comprising a polycarbonic acid-based copolymer in an amount of 0.001 to 5.0 parts by weight and a surface crosslinking agent in an amount of 0.001 to 5.0 parts by weight, based on 100 parts by weight of the superabsorbent base resin.

Also contemplated in accordance with a further aspect of the present disclosure is a method for preparing a surface-modified superabsorbent polymer, comprising:

a) providing a superabsorbent base resin;

b) preparing a mixture solution comprising a water-soluble polyvalent cationic salt in an amount of 0.001 to 5.0 parts by weight, a polycarbonic acid-based copolymer in an amount of 0.001 to 5.0 parts by weight, and a surface crosslinking agent in an amount of 0.001 to 5.0 parts by weight, based on 100 parts by weight of the superabsorbent base resin; and c) subjecting the superabsorbent bas resin of step a) to surface crosslinking with the mixture solution of step b).

Advantageous Effects

Compared to conventional SAPs, the SAPs prepared by surface crosslinking treatment with a water-soluble polyvalent cationic salt, a polycarbonic acid-based copolymer, and a surface crosslinking agent in accordance with the present disclosure are greatly improved in permeability even though using neither silica nor an organic solvent, which results in an effective reduction in process time and cost. Thus, the SAPs of the present disclosure enjoy the advantage of improving in processability sufficiently to decrease a load and to readily control particle size distribution and physical properties, and minimizing the property degradation attributed to the breakdown of the resin in applied processing.

BEST MODE

Below, a detailed description will be given of the present disclosure.

In accordance with an aspect thereof, the present disclosure addresses a superabsorbent polymer with a surface crosslink-treated with a water-soluble polyvalent cationic salt, a polycarbonic acid-based copolymer, and a surface crosslinking agent.

In some embodiments, the water-soluble polyvalent cationic salt may be contained in an amount of 0.001 to 5.0 parts by weight, based on 100 parts by weight of the superabsorbent base resin. Within this content range, the water-soluble polyvalent cationic salt allows the superabsorbent polymer to increase in permeability without causing a significant degradation of other properties.

In the water-soluble salt, the polyvalent cationic ion may be selected from the group consisting of $Al^{3+}$, $Zr^{4+}$, $Sc^{3+}$, $Ti^{4+}$, $V^{5+}$, $CR^{3+}$, $Mn^{2+}$, $Fe^{3+}$, $Ni^{2+}$, $Cu^{2+}$, $Zn^{2+}$, $Ag^+$, $Pt^{4+}$, $Au^+$, and a combination thereof while the counterpart anion may be selected from the group consisting of sulfate ($SO_4^{2-}$), sulfite ($SO_3^{2-}$), nitrate ($NO^{3-}$), metaphosphate ($PO^{3-}$), phosphate ($PO_4^{3-}$), and a combination thereof. The water-soluble salt may be particularly aluminum sulfate ($Zr(SO_4)_2$) and more particularly zirconium sulfate ($Zr(SO_4)_2$), and may be in the form of a hydrate.

Figure 3:
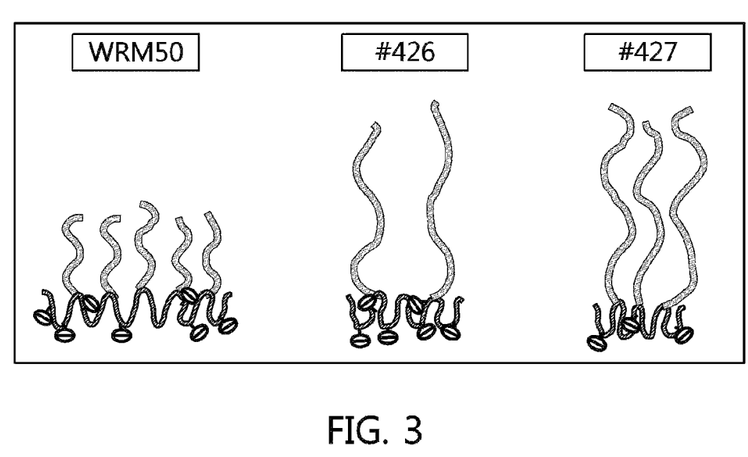
FIG. 3 is a schematic diagram showing chemical structures of polycarbonic acid-based copolymers WRM50, #426, and #427.

The polycarbonic acid-based copolymer may act as a superplasticizer in the superabsorbent polymer, and has a structure in which a main chain is conjugated with a plurality of side chains or branches, like a comb, as shown in FIG. 3.

According to some embodiments, the polycarbonic acid-based copolymer consists of a main chain having a (meth)acrylic acid-based monomer as a structural unit; and a side chain composed of an alkoxypolyalkylene glycol mono (meth)acrylic acid ester monomer. Preferably, the polycarbonic acid-based copolymer is contained in an amount of 0.001 to 5.0 parts by weight, based on 100 parts by weight of the superabsorbent base resin. When used after treatment of the superabsorbent polymer with the water-soluble polyvalent cationic salt, the polycarbonic acid-based copolymer in the content range can allow the superabsorbent polymer to improve in permeability as well as to retain still high processability, without a significant degradation of other properties.

In a particular embodiment, the polycarbonic acid-based copolymer may contain 50 to 99% by weight of the alkoxypolyalkylene glycol mono(meth)acrylic acid ester monomer and 1 to 50% by weight of the (meth)acrylic acid monomer.

With the monomers in such ranges, the copolymer is advantageous in exerting excellent dispersibility, slump retention, and initial dispersibility, as well as in expressing appropriate air entrainment.

The alkoxypolyalkylene glycol mono(meth)acrylic acid ester monomer that serves as a side chain of the polycarbonic acid-based copolymer may be represented by the following Chemical Formula 1:

[Chemical Formula 1]

wherein, $R^1$ is a hydrogen atom or methyl;

$R^2O$ represents an oxyalkylene moiety of 2 to 4 carbon atoms;

$R^3$ is alkyl of 1 to 4 carbon atoms; and m is an integer of 50 to 200, expressing an average addition mole number of oxyalkylene.

When the average addition mole number of oxyalkylene ranges from 50 to 200, the side chain guarantees excellent dispersibility and slump retention. In a particular embodiment, the average addition mole number of oxyalkylene may be between 50 to 150.

The alkoxy polyalkylene glycol mono(meth)acrylic acid ester monomer may be at least one selected from the group consisting of methoxypolyethylene glycol mono(meth)acrylate, methoxypolypropylene glycol mono(meth)acrylate, methoxypolybutylene glycol mono(meth)acrylate, methoxypolyethylene glycol polypropylene glycol mono (meth)acrylate, methoxypolyethylene glycol polybutylene glycol mono(meth)acrylate, methoxypolypropylene glycol polybutylene glycol mono(meth)acrylate, methoxypolyethylene glycol polypropylene glycol polybutylene glycol mono(meth)acrylate, ethoxypolyethylene glycol mono (meth)acrylate, ethoxypolypropylene glycol mono(meth) acrylate, ethoxypolybutylene glycol mono(meth)acrylate, ethoxypolyethylene glycol polypropylene glycol mono (meth)acrylate, ethoxypolyethylene glycol polybutylene glycol mono(meth)acrylate, ethoxypolypropylene glycol polybutylene glycol mono(meth)acrylate, and ethoxypolyethylene glycol polypropylene glycol polybutylene glycol mono(meth)acrylate.

The (meth)acrylic acid monomer that serves as a structural unit of the main chain of the polycarbonic acid-based copolymer may be represented by the following Chemical Formula 2:

[Chemical Formula 2]

wherein, $R^2$ is an unsaturated hydrocarbon of 2 to 5 carbon atoms; and $M^1$ is a hydrogen atom, a monovalent or divalent metal, an ammonium group, or an organic amine group.

The (meth)acrylic acid monomer of Chemical Formula 2 may be at least one selected from the group consisting of an acrylic acid, a methacrylic acid, a monovalent or divalent metal salt thereof, an ammonium salt thereof, and an organic amine salt thereof.

The polycarbonic acid-based copolymer may be prepared by copolymerizing the monomers in the presence of a polymerization initiator. Copolymerization may be carried out by solution polymerization or bulk polymerization, but is not limited thereto.

By way of example, when polymerization is performed with water as a solvent, a water-soluble polymerization initiator, such as ammonium, alkali metal persulfate, or hydrogen peroxide may be employed. Solution polymerization in a solvent such as a lower alcohol, an aromatic hydrocarbon, an aliphatic hydrocarbon, an ester compound or a ketone compound may employ as a polymerization initiator a peroxide, such as benzoylperoxide, lauroylperoxide, or cumen hydroperoxide, or an aromatic azo compound such as azobisisobutyronitrile. In this regard, an accelerator such as an amine compound may be used in combination.

For polymerization in a water-lower alcohol mixture solvent, an eligible combination of the various polymerization initiators and optionally the accelerator may be used.

The polymerization initiator may be used in an amount of 0.5% to 5% by weight, based on the total weight of the monomer mixture employed while the polymerization temperature may be set depending on the kind of the solvent or the polymerization initiator, and may range from 0° C. to 120° C.

In order to control the molecular weight of the polycarbonic acid-based copolymer, a thiol-based chain transfer agent may be added. The thiol-based chain transfer agent may be at least one selected from the group consisting of mercapto ethanol, thioglycerol, thioglycolic acid, 2-mercapto propionic acid, 3-mercapto propionic acid, thiomalic acid, thioglycolic acid octyl, and 3-mercapto propionic acid octyl, and may be used in an amount of 0.01% to 5% by weight, based on the total weight of the monomer mixture.

In a particular embodiment, the polycarbonic acid-based copolymer or a neutralized salt thereof may range in weight average molecular weight from 30,000 to 70,000 and preferably from 40,000 to 60,000 in consideration of dispersibility, as measured by GPC (Gel Permeation Chromatography).

In some embodiments of the present disclosure, #427 polycarbonic acid-based copolymer, a novel polymer derived from the commercially available polycarbonic acid-based copolymer WRM 50 (LG Chem) by alteration in side chain length and chain density, is used for the surface crosslinking modification leading to an improvement in property. For reference, #427 is identical to WRM50 with the exception that the molecular weight (length) of the alkoxypolyalkylene glycol mono(meth)acrylic acid ester monomer as a side chain is changed.

In Table 1, below, the polycarbonic acid-based copolymers WRM50, #426, and #427 are described for their basic properties including TSC (Total solid content: %), pH, and viscosity (25° C.), and results of GPC analysis are also listed. In addition, as shown in FIG. 3, the polycarbonic acid-based copolymers differ in structural features from one to another. The side chain alkoxypolyalkylene glycol mono (meth)acrylic acid ester monomer is longer (heavier) in #426 and #427 than WRM50, with a higher density of the side chain for #427 than #426.

TABLE 1

Properties of Three PCEs WRM50, #426, and #427

Basic Properties

| | TSC (%) | pH | Vis. (25° C.) |
|---|---|---|---|
| WRM50 | 50.34 | 4.9 | 334 |
| #426 | 44.71 | 5.06 | 307 |
| #427 | 44.12 | 4.88 | 204 |

GPC Result

| Sample | Mw | PDI | Low-Mw (%) |
|---|---|---|---|
| WRM50 | 40,654 | 1.94 | 17.7 |
| #426 | 27,780 | 2.18 | 4.2 |
| #427 | 16,911 | 1.81 | 5.9 |

Further, analysis for the particle size distribution of SAPs showed that the SAPs retained processability even after being subjected to surface crosslinking treatment with the polycarbonic acid-based copolymer. It was also demonstrated that SAPs were provided with more improved physical properties when the surface crosslinking treatment was carried out with a combination of the polycarbonic acid-based copolymer and the water-soluble polyvalent cationic salt than with the polycarbonic acid-based copolymer alone. Particularly in the present disclosure, a surface crosslinking agent such as ethylene carbonate is applied to the base resin, which is defined as a superabdorbent polymer before surface crosslinking, in the absence of an organic solvent such as methanol, which leads to the significance of greatly reducing process time and cost and improving physical properties.

For reference, SAPs on the surface of which crosslinking treatment has been conducted with an organic solvent such as methanol may produce odors later. Studies are thus now ongoing on the surface crosslinking in the absence of an organic solvent.

The surface crosslinking agent is responsible for a crosslinking reaction on the surface of the SAPs. The surface crosslinking agent may be used in an amount of 0.001 to 5.0 parts by weight, based on 100 parts by weight of the superabsorbent base resin, preferably in an amount of 0.001 to 3.0 parts by weight, and in an amount of 0.05 to 2.0 parts by weight. If too little of the surface crosslinking agent is used, only slight surface crosslinking reaction may occur. On the other hand, the presence of the surface crosslinking agent in an amount exceeding 5.0 parts by weight based on 100 parts by weight of the superabsorbent base resin induces an excessive surface crosslinking reaction, rather degrading physical properties of the SAPs.

Any surface crosslinking agent that reacts with a functional group of the polymer can be employed without limitations to the configuration thereof in the method for preparing SAPs according to the present disclosure. Preferably to enhance properties of the SAPs thus prepared, the surface crosslinking agent may be selected from the group consisting of a polyhydric compound; an epoxy compound; a polyamine compound; a haloepoxy compound; a haloepoxy compound condensate; an oxazoline compound; a mono-, di- or polyoxazolidinone compound; a cyclic urea compound; a multi-valent metal salt; an alkylene carbonate compound; and a combination thereof.

Concrete examples of the polyhydric alcohol compound include mono-, di-, tri-, tetra- or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

The epoxy compound may be ethylene glycol diglycidyl ether or glycidol. The polyamine compound may be selected from the group consisting of ethylene diamine, diethylene triamine, triethylene tetramine, tetraethylene pentamine, pentaethylene hexamine, polyethylene imine, polyamide polyamine, and a combination thereof.

Epichlorohydrin, epibromohydrin, and α-methylepichlorohydrin may fall within the scope of the haloepoxy compound useful as a surface crosslinking agent. The mono-, di- or polyoxazolidinone compound may be exemplified by 2-oxazolidinone.

Ethylene carbonate may be representative of the alkylene carbonate compound. These compounds may be used alone or in combination. In order to enhance the efficiency of the surface crosslinking process, the surface crosslinking agent preferably includes at least one polyhydric alcohol compound, and more preferably a polyhydric alcohol compound of 2 to 10 carbon atoms.

In the preparation of the surface-crosslinked superabsorbent polymer of the present disclosure, as described above, the surface crosslinking may be achieved by treating the superabsorbent base resin with the water-soluble polyvalent cationic salt, and then with a mixture of the polycarbonic acid-based copolymer and the surface crosslinking agent (e.g., alkylene carbonate) (2-step), or by treating the superabsorbent base resin with a mixture of the water-soluble polyvalent cationic salt, the polycarbonic acid-based copolymer, and the surface crosslinking agent (e.g., alkylene carbonate) (1-step). The surface-crosslinked superabsorbent polymer, whether prepared in the 2-step process or the 1-step process, is found to still retain high processability.

The method may further comprise milling the surface-crosslinked superabsorbent polymer, and classifying the milled superabsorbent polymer by particle size into particles with sizes of less than 150 μm, from 150 μm to less than 300 μm, from 300 μm to less than 600 μm, from 600 μm to 850 μm, and greater than 850 μm. The milling step may be carried out with a mill the examples of which include, but are not limited to, a ball mill, a pin mill, a hammer mill, a screw mill, a roll mill, a disc mill, and a jog mill The surface-crosslinked superabsorbent polymer of the present disclosure, when treated with a mixture of the water-soluble polyvalent cationic salt, the polycarbonic acid-based copolymer, and the surface crosslinking agent (e.g., alkylene carbonate) was observed to advance much in permeability, compared to conventional SAPs, even though neither silica nor an organic solvent is employed.

The superabsorbent base resin is prepared by a method comprising:

a) polymerizing a monomer composition containing a water-soluble ethylenically unsaturated monomer and a polymerization initiator by heat or light to give a hydrogel phase polymer;

b) drying the hydrogel phase polymer; and c) milling the dried hydrogel phase polymer into superabsorbent polymer particles.

As used herein, the term "superabsorbent base resin" refers to particles obtained by drying and milling the hydrogel phase polymer. In greater detail, the hydrogel phase polymer has a jelly form 1 cm or larger in size with a high water content (50% or higher) after completion of the polymerization, and is dried and milled into powders. That is, the superabsorbent base resin is a pre-crosslinking superabsorbent polymer, and thus the hydrogel phase polymer corresponds to a product in a meso-phase of the method.

The preparation of a superabsorbent base resin in accordance with the present disclosure starts with a) thermal polymerization or photopolymerization of water-soluble, ethylenically unsaturated monomers to a hydrogel phase polymer in the presence of a polymerization initiator.

For this, steps or processes typical in the art may be employed. In detail, the polymerization initiator contained in the monomer composition for use in the preparation of the superabsorbent base resin of the present disclosure may depend on the type of polymerization. That is, either a photopolymerization initiator or a thermal polymerization initiator may be used. For photopolymerization, however, heat is generated not only by UV light irradiation, but also by the polymerization, which is an exothermic reaction. Hence, a thermal polymerization initiator may be additionally contained even upon photopolymerization.

Although no special limitations are imparted thereto, the thermal polymerization initiator useful in the method for the preparation of the superabsorbent base resin according to the present disclosure may be preferably selected from the group consisting of a persulfate salt, an azo compound, hydrogen peroxide, ascorbic acid, and a combination thereof. Examples of the perfulate initiator include sodium persulfate ($Na_2S_2O_8$), potassium persulfate ($K_2S_2O_8$), and ammonium persulfate (($NH_4)_2S_2O_8$). Among the azo compound useful as a thermal polymerization initiator in the preparation of the preparation of the superabsorbent base resin according to the present disclosure are 2, 2-azobis(2-amidinopropane) dihydrochloride, 2,2-azobis-(N, N-dimethylene)isobutyramidine dihydrochloride, 2-(carbamoylazo)isobutyronitrile), 2,2-azobis[2-(2-imidazolin-2-yl) propane] dihydrochloride, and 4,4-azobis-(4-cyanovaleric acid).

The photopolymerization initiator available in the method for the preparation of the superabsorbent base resin according to the present disclosure, although not specifically limited, may be preferably selected from the group consisting of benzoin ether, dialkyl acetophenone, hydroxyl alkylketone, phenyl glyoxylate, benzyl dimethyl ketal, acyl phosphine, α-aminoketone, and a combination thereof. As an acyl phosphine, commercially available lucirin TPO, that is, 2, 4, 6-trimethyl-benzoyl-trimethyl phosphine oxide may be used.

So long as it is typically used in the preparation of SAPs, any water-soluble, ethylenically unsaturated monomer may be used without limitations in the preparation method of the superabsorbent base resin according to the present disclosure. Preferably, the water-soluble, ethylenically unsaturated monomer may be selected from the group consisting of an anionic monomer or a salt thereof, a non-ionic hydrophilic monomer, an amino group-containing unsaturated monomer and a quaternary salt thereof, and a combination thereof. Examples of the water-soluble, ethylenically unsaturated monomer include anionic monomers or salts thereof, such as acrylic acid, methacrylic acid, anhydrous maleic acid, fumaric acid, crotonic acid, itaconic acid, 2-acryloylethanesulfonic acid, 2-methacryloylethanesulfonic acid, 2-(meth) acryloylpropanesulfonic acid, and 2-(meth)acrylamide-2-methylpropane sulfonic acid; non-ionic hydrophilic monomers, such as (meth)acrylamide, N-substituted (meth) acrylate, 2-hydroxyethyl (meth)acrylate, 2-hydroxypropyl (meth)acrylate, methoxypolyethylene glycol (meth)acrylate, and polyethylene glycol (meth)acrylate; and an amino group-containing unsaturated monomers or quaternary salts thereof, such as (N, N)-dimethylaminoethyl (meth)acrylate, and (N, N)-dimethylaminopropyl (meth)acrylamide, with preference for an acrylic acid or a salt thereof. Advantageously from acrylic acid or a salt thereof, SAPs that are particularly improved in absorbency can be obtained.

For resource recycling, micro- or submicro-particles of the prepared SAPs, that is, the prepared superabsorbent base resin with a particle size of less than 150 μm, may be contained in the monomer composition during the preparation of the superabsorbent base resin according to the present disclosure. In detail, the polymer particles with a particle size of less than 150 μm may be added to the monomer composition before the polymerization reaction or to the reaction mixture at an initial, middle, or late phase of the polymerization. No limitations are imparted to the amount of the superabsorbent polymer powder. Preferably, it is added in an amount of 1 to 10 parts by weight, based on 100 parts by weight of the monomer composition, in terms of preventing physical properties of the final superabsorbent base resin from deteriorating.

In the method for preparing a superabsorbent base resin in accordance with the present disclosure, the content of the water-soluble ethylenically unsaturated monomer in the monomer composition may be properly determined in consideration of polymerization time and reaction conditions, and may preferably range from 40 to 55% by weight. Less than 40% by weight of the water-soluble ethylenically unsaturated monomer is economically disadvantageous. When the monomer is used in an amount exceeding 55% by weight, the resulting hydrogel phase polymer may be milled at a low rate.

So long as it is typically used for thermal polymerization or photopolymerization in the art, any technique may be applied without limitations to the preparation of a hydrogel phase polymer from the monomer composition. Largely, polymerization is divided into thermal polymerization and photopolymerization according to energy source. On the whole, thermal polymerization may be performed in a reactor installed with a stirring shaft, such as a kneader. For photopolymerization, a conveyer belt may run under a light source in a reactor. These techniques are illustrated as exemplary embodiments, but are not to be construed to limit the present disclosure.

For example, a hydrogel phase polymer is prepared in a reactor installed with a stirring shaft, such as a kneader, by thermal polymerization, e.g., by providing hot air to the reactor or by heating the reactor, and discharged from the reactor as particles millimeters to centimeters long according to the type of the stirring shaft. In detail, the size of the obtained hydrogel phase polymer particles may vary depending on the concentration and feeding rate of the monomer composition, and typically ranges from 2 to 50 mm In addition, when photopolymerization is performed on a movable conveyer belt as mentioned above, the resulting hydrogel phase polymer may typically take a sheet-like form with a width equal to that of the belt. The polymer sheet may vary in thickness depending on the concentration and feeding rate of the monomer composition. The monomer composition is preferably fed such that a sheet-like polymer with a thickness of 0.5 to 5 cm may be obtained. A feeding condition of the monomer composition that affords too thin a polymer sheet may result in low productivity. When the thickness of the sheet-like polymer exceeds 5 cm, the polymerization reaction may not occur evenly throughout the entire thickness.

The light source available in the photopolymerization step is not imparted with special limitations. Any UV light that causes a photopolymerization reaction may be employed. For example, light with a wavelength of 200 to 400 nm, or a UV light source such as that from a Xe lamp, a mercury lamp, or a metal halide lamp may be used. The photopolymerization may be performed for approximately 5 sec to approximately 10 min under a light intensity of approximately 0.1 mw/cm$^2$ to approximately 1 kw/cm$^2$. When the light intensity is too low or the irradiation time is too short, insufficient polymerization reactions may result. On the other hand, too high a light intensity or too long an irradiation time may cause a poor quality of the superabsorbent polymers.

Next, step b) of drying the hydrogel phase polymer is carried out in the method for preparing a superabsorbent base resin in accordance with the present disclosure.

The hydrogel phase polymer obtained in step a) has a water content of 30 to 60% by weight. As used herein, the term "water content" refers to weight percentage of water to the total weight of the hydrogel phase polymer. The amount of water may be obtained by subtracting the weight of dried polymer from the total weight of the hydrogel phase polymer (in detail, after the polymer is dried by infrared heating, the mass loss attributed to moisture evaporation is measured. The drying condition is such that the atmosphere is heated from room temperature to 180° C. and maintained at 180° C., with a total drying time set to be 20 min including 5 min for the temperature increment).

The hydrogel phase polymer obtained in step a) undergoes a drying process. Preferably, the drying may be conducted at 150° C. to 250° C. The term "drying temperature", as used herein, means the temperature of a heat medium provided for drying or the temperature of a dryer including a heat medium and the polymer therein.

A drying temperature of less than 150° C. may make the drying time long, and is apt to degrade properties of the final SAPs. When the drying temperature exceeds 250° C., there is high likelihood that only the surface of the polymer is dried, which leads to the generation of fine powder in a subsequent milling step, and the degradation of properties of the final SAPs. Preferably, the drying may be conducted at 150° C. to 250° C., and more particularly at 160° C. to 200° C.

As for the drying time, its configuration is not specifically limited, and may be set to range from 20 to 90 min in consideration of process efficiency.

Any drying process that is typically used to dry hydrogel phase polymers may be selected, without limitations to the configuration thereof. In detail, the drying step may be conducted by supplying hot air, or irradiating with IR light, microwaves, or UV light. After the drying step, the water content of the polymer may be decreased to 0.1 to 10% by weight.

In advance of the drying step, as needed, the method for preparing SAPs in accordance with the present disclosure may further comprise briefly crushing the hydrogel phase polymer to enhance the efficiency of the drying step. In this brief crushing step, the hydrogel phase polymer may be crushed into particles with a size of 1 mm to 15 mm. It is technically difficult to crush the polymer into particles less than 1 mm in size due to the high water content of the hydrogel phase polymer. Even though possible to crush the polymer into particles less than 1 mm in size, the crushed particles are prone to agglomeration therebetween. On the other hand, crushed particles with a size of greater than 15 mm do not guarantee the subsequent drying step will be efficient.

For use in the brief crushing step prior to the drying step, a crushing machine may be employed without limitations to the configuration thereof. Examples of the crushing machine include, but are not limited to, a vertical pulverizer, a turbo cutter, a turbo grinder, a rotary cutter mill, a cutter mill, a disc mill, a shred crusher, a crusher, a chopper, and a disc cutter.

When a crushing step is carried out to enhance the drying efficiency in the subsequent drying step, the hydrogel phase polymer may be likely to adhere to the surface of the crusher due to its high water content. To increase the efficiency of the pre-drying crushing step, an additive preventive of the adherence of the hydrogel phase polymer to the crusher may be employed. Examples of the additive available for preventing the adherence include a powder aggregation preventer such as steam, water, a surfactant, or inorganic powder, e.g., clay or silica; a thermal polymerization initiator, such as a persulfate initiator, an azo-type initiator, hydrogen peroxide, and ascorbic acid; a crosslinking agent, such as an epoxy-based crosslinking agent, a diol-containing crosslinking agent, a crosslinking agent containing acrylate of multifunctionality, e.g., bi- or tri-functionality, and a mono-functional compound containing a hydroxide group, but are not limited thereto.

After the drying step, the method for preparing a superabsorbent base resin according to the present disclosure proceeds to c) milling the dried hydrogel phase polymer into particles. The polymer particles obtained in the milling step have a particle size of 150 to 850 µm. The milling step of the method for preparing a superabsorbent base resin according to the present disclosure may be achieved with a mill the examples of which include, but are not limited to, a pin mill, a hammer mill, a screw mill, a roll mill, a disc mill and a jog mill.

In accordance with another aspect thereof, the present disclosure addresses a method for preparing a surface-crosslinked superabsorbent polymer, comprising:
a) providing a superabsorbent base resin;
b) pre-treating the superabsorbent base resin of step a) by mixing a water-soluble polyvalent cationic salt in an amount of 0.001 to 5.0 parts by weight, based on 100 parts by weight of the superabsorbent base resin provided in step a); and
c) subjecting the pre-treated superabsorbent base resin of step b) to surface crosslinking with a mixture solution comprising a polycarbonic acid-based copolymer in an amount of 0.001 to 5.0 parts by weight and a surface crosslinking agent in an amount of 0.001 to 5.0 parts by weight, based on, based on 100 parts by weight of the superabsorbent base resin.

Also contemplated in accordance with a further aspect of the present disclosure is a method for preparing a surface-modified superabsorbent polymer, comprising:
a) providing a superabsorbent base resin;
b) preparing a mixture solution comprising a water-soluble polyvalent cationic salt in an amount of 0.001 to 5.0 parts by weight, a polycarbonic acid-based copolymer in an amount of 0.001 to 5.0 parts by weight, and a surface crosslinking agent in an amount of 0.001 to 5.0 parts by weight, based on 100 parts by weight of the superabsorbent base resin; and
c) subjecting the superabsorbent bas resin of step a) to surface crosslinking with the mixture solution of step b).

In some embodiments, the water-soluble polyvalent cationic salt may be used in an amount of 0.001 to 5.0 parts by weight, based on 100 parts by weight of the superabsorbent resin. Within this content range, the water-soluble polyvalent cationic salt can allow the superabsorbent polymer to increase in permeability without causing a significant degradation of other properties.

In the water-soluble salt, the polyvalent cationic ion may be selected from the group consisting of $Al^{3+}$, $Zr^{4+}$, $Sc^{3+}$, $Ti^{4+}$, $V^{5+}$, $CR^{3+}$, $Mn^{2+}$, $Fe^{3+}$, $Ni^{2+}$, $Cu^{2+}$, $Zn^{2+}$, $Ag_+$, $Pt^{4+}$, $Au^+$, and a combination thereof while the counterpart anion may be selected from the group consisting of sulfate ($SO_4^{2-}$), sulfite ($SO_3^{2-}$), nitrate ($NO^{3-}$), metaphosphate ($PO^{3-}$), phosphate ($PO_4^{3-}$), and a combination thereof. The water-soluble salt may be particularly aluminum sulfate ($Zr(SO_4)_2$) and more particularly zirconium sulfate ($Zr(SO_4)_2$), and may be in the form of a hydrate.

The polycarbonic acid-based copolymer may act as a superplasticizer in the superabsorbent polymer, and has a structure in which a main chain is conjugated with a plurality of side chains or branches, like a comb, as shown in FIG. 3.

According to some embodiments, the polycarbonic acid-based copolymer consists of a main chain having a (meth)acrylic acid-based monomer as a structural unit; and a side chain composed of an alkoxypolyalkylene glycol mono(meth)acrylic acid ester monomer. Preferably, the polycarbonic acid-based copolymer is contained in an amount of 0.001 to 5.0 parts by weight, based on 100 parts by weight of the superabsorbent polymer. When used after treatment of the superabsorbent polymer with the water-soluble polyvalent cationic salt, the polycarbonic acid-based copolymer in the content range causes the superabsorbent polymer to improve in permeability as well as to retain still high processability, without a significant degradation of other properties.

In a particular embodiment, the polycarbonic acid-based copolymer may contain 50 to 99% by weight of the alkoxypolyalkylene glycol mono(meth)acrylic acid ester monomer and 1 to 50% by weight of the (meth)acrylic acid monomer.

With the monomers in such ranges, the copolymer is advantageous to exert excellent dispersibility, slump retention, and initial dispersibility, and to express appropriate air entrainment.

The alkoxypolyalkylene glycol mono(meth)acrylic acid ester monomer that serves as a side chain of the polycarbonic acid-based copolymer may be represented by the following Chemical Formula 1:

[Chemical Formula 1]

wherein,
$R^1$ is a hydrogen atom or methyl;
$R^2O$ represents an oxyalkylene moiety of 2 to 4 carbon atoms;
$R^3$ is alkyl of 1 to 4 carbon atoms; and
m is an integer of 50 to 200, expressing an average addition mole number of oxyalkylene.

When the average addition mole number of oxyalkylene ranges from 50 to 200, the side chain guarantees excellent dispersibility and slump retention. In a particular embodiment, the average addition mole number of oxyalkylene may be between 50 to 150.

The alkoxy polyalkylene glycol mono(meth)acrylic acid ester monomer may be at least one selected from the group consisting of methoxypolyethylene glycol mono(meth)acrylate, methoxypolypropylene glycol mono(meth)acrylate, methoxypolybutylene glycol mono(meth)acrylate, methoxypolyethylene glycol polypropylene glycol mono(meth)acrylate, methoxypolyethylene glycol polybutylene glycol mono(meth)acrylate, methoxypolypropylene glycol polybutylene glycol mono(meth)acrylate, methoxypolyethylene glycol polypropylene glycol polybutylene glycol mono(meth)acrylate, ethoxypolyethylene glycol mono(meth)acrylate, ethoxypolypropylene glycol mono(meth)acrylate, ethoxypolybutylene glycol mono(meth)acrylate, ethoxypolyethylene glycol polypropylene glycol mono(meth)acrylate, ethoxypolyethylene glycol polybutylene glycol mono(meth)acrylate, ethoxypolypropylene glycol polybutylene glycol mono(meth)acrylate, and ethoxypolyethylene glycol polypropylene glycol polybutylene glycol mono(meth)acrylate.

The (meth)acrylic acid monomer that serves as a structural unit of the main chain of the polycarbonic acid-based copolymer may be represented by the following Chemical Formula 2:

$$R^2—COOM^1 \quad \text{[Chemical Formula 2]}$$

wherein, $R^2$ is an unsaturated hydrocarbon of 2 to 5 carbon atoms; and $M^1$ is a hydrogen atom, a monovalent or divalent metal, an ammonium group, or an organic amine group.

The (meth)acrylic acid monomer of Chemical Formula 2 may be at least one selected from the group consisting of an acrylic acid, a methacrylic acid, a monovalent or divalent metal salt thereof, an ammonium salt thereof, and an organic amine salt thereof.

The polycarbonic acid-based copolymer may be prepared by copolymerizing the monomers in the presence of a polymerization initiator. Copolymerization may be carried out by solution polymerization or bulk polymerization, but is not limited thereto.

For example, when polymerization is performed with water as a solvent, a water-soluble polymerization initiator, such as ammonium, alkali metal persulfate, or hydrogen peroxide, may be employed. Solution polymerization in a solvent such as a lower alcohol, an aromatic hydrocarbon, an aliphatic hydrocarbon, an ester compound or a ketone compound may employ as a polymerization initiator a peroxide, such as benzoylperoxide, lauroylperoxide, or cumen hydroperoxide, or an aromatic azo compound such as azobisisobutyronitrile. In this regard, an accelerator such as an amine compound may be used in combination.

For polymerization in a water-lower alcohol mixture solvent, an eligible combination of the various polymerization initiators and optionally the accelerator may be used.

The polymerization initiator may be used in an amount of 0.5% to 5% by weight, based on the total weight of the monomer mixture employed while the polymerization temperature may be set depending on the kind of the solvent or the polymerization initiator, and may range from 0° C. to 120° C.

In order to control the molecular weight of the polycarbonic acid-based copolymer, a thiol-based chain transfer agent may be added. The thiol-based chain transfer agent may be at least one selected from the group consisting of mercapto ethanol, thioglycerol, thioglycolic acid, 2-mercapto propionic acid, 3-mercapto propionic acid, thiomalic acid, thioglycolic acid octyl, and 3-mercapto propionic acid octyl, and may be used in an amount of 0.01% to 5% by weight, based on the total weight of the monomer mixture.

In a particular embodiment, the polycarbonic acid-based copolymer or a neutralized salt thereof may range in weight average molecular weight from 30,000 to 70,000 and preferably from 40,000 to 60,000 in consideration of dispersibility, as measured by GPC (Gel Permeation Chromatography).

According to some embodiments of the present disclosure, #427 polycarbonic acid-based copolymer, a novel polymer derived from the commercially available polycarbonic acid-based copolymer WRM 50 (LG Chem) by alteration in side chain length and chain density, is used for the surface crosslinking modification leading to an improvement in property. For reference, #427 is identical to WRM50 with the exception that the molecular weight (length) of the alkoxypolyalkylene glycol mono(meth)acrylic acid ester monomer as a side chain is changed.

In Table 1, the polycarbonic acid-based copolymers WRM50, #426, and #427 are described for their basic properties including TSC (Total solid content:%), pH, and viscosity (25° C.), and results of GPC analysis are also listed. In addition, as shown in FIG. 3 and Table 2, the polycarbonic acid-based copolymers differ in structural features from one to another. The side chain alkoxypolyalkylene glycol mono(meth)acrylic acid ester monomer is longer (heavier) in #426 and #427 than WRM50, with a higher density of side chains for #427 than #426

TABLE 2

| Polymer | Performance | Main Chain | Side Chain | Density of side chain |
|---------|-------------|------------|------------|----------------------|
| WRM50 | Low dispersion Low retention | Long | Short | High |
| #426 | High dispersion | Short | Long | Low |
| #427 | High dispersion High retention | Very short | Long | High |

Further, analysis for the particle size distribution of SAPs showed that SAPs retained processability even after being subjected to surface crosslinking modification with the polycarbonic acid-based copolymer. It was also demonstrated that SAPs were provided with further improved physical properties when the surface crosslinking modification was carried out with a combination of the polycarbonic acid-based copolymer and the water-soluble polyvalent cationic salt than with the polycarbonic acid-based copolymer alone. Particularly in the present disclosure, a surface crosslinking agent such as ethylene carbonate is applied to the base resin, which is defined as a superabdorbent polymer, before surface crosslinking, in the absence of an organic solvent such as methanol, which leads to greatly reducing process time and cost, and improving physical properties.

For reference, SAPs on the surface of which crosslinking treatment has been conducted with an organic solvent such as methanol may produce odors later. Studies are thus now ongoing on the surface crosslinking in the absence of an organic solvent.

The surface crosslinking agent is responsible for a crosslinking reaction on the surface of the SAPs. The surface crosslinking agent may be used in an amount of 0.001 to 5.0 parts by weight, based on 100 parts by weight of the superabsorbent base resin, preferably in an amount of 0.001 to 3.0 parts by weight, and in an amount of 0.05 to 2.0 parts by weight. If too little the surface crosslinking agent is used, only slight surface crosslinking reaction may occur. On the other hand, the presence of the surface crosslinking agent in an amount exceeding 5.0 parts by weight based on 100 parts by weight of the superabsorbent base resin induces an excessive surface crosslinking reaction, rather degrading physical properties of the SAPs.

Any surface crosslinking agent that reacts with a functional group of the polymer can be employed without limitations to the configuration thereof in the method for preparing SAPs according to the present disclosure. Preferably to enhance properties of the SAPs thus prepared, the surface crosslinking agent may be selected from the group consisting of a polyhydric compound; an epoxy compound; a polyamine compound; a haloepoxy compound; a haloepoxy compound condensate; an oxazoline compound; a mono-, di- or polyoxazolidinone compound; a cyclic urea compound; an alkylene carbonate compound; and a combination thereof.

Concrete examples of the polyhydric alcohol compound include mono-, di-, tri-, tetra- or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

The epoxy compound may be ethylene glycol diglycidyl ether or glycidol. The polyamine compound may be selected from the group consisting of ethylene diamine, diethylene triamine, triethylene tetramine, tetraethylene pentamine, pentaethylene hexamine, polyethylene imine, polyamide polyamine, and a combination thereof.

Epichlorohydrin, epibromohydrin, and α-methylepichlorohydrin may fall within the scope of the haloepoxy compound useful as a surface crosslinking agent. The mono-, di- or polyoxazolidinone compound may be exemplified by 2-oxazolidinone.

Ethylene carbonate may be representative of the alkylene carbonate compound. These compounds may be used alone or in combination. In order to enhance the efficiency of the surface crosslinking process, the surface crosslinking agent preferably includes at least one polyhydric alcohol compound, and more preferably a polyhydric alcohol compound of 2 to 10 carbon atoms.

No limitations are imposed on the modality of adding the surface crosslinking agent to the superabsorbent base resin. For example, the surface crosslinking agent may be mixed with the superabsorbent base resin in a reactor, sprayed on the superabsorbent base resin, or fed, together with the superabsorbent base resin, to a reactor that continuously operates, such as a mixer.

The surface crosslinking modification may be conducted at 100 to 300° C. for 1 to 90 min. Within this relatively high temperature range, the surface crosslinking modification can be improved in efficiency, minimizing the content of remaining monomers in the final SAPs and providing excellent properties for the final SAPs. Throughout the specification, a temperature for surface crosslinking modification is defined as the overall temperature of the surface cros slinking agent and the polymer.

In the preparation method of surface-crosslinked superabsorbent polymers according to the present invention, a crosslinking reaction may be conducted for 1 to 90 min and preferably for 5 to 60 min after a temperature is elevated for the crosslinking reaction. A crosslinking reaction time of less than 1 min may not elicit a sufficient crosslinking reaction. On the other hand, when a crosslinking reaction time exceeds 90 min, an excessive surface crosslinking reaction may occur, rather degrading physical properties of the SAPs and structurally destroying the SAP due to the lengthy retention in the reactor.

No particular limitations are imparted on a means for elevating a temperature for surface crosslinking modification. For instance, a heat medium may be supplied, or direct heating may be performed with, e.g., electricity, but the present invention is not limited thereto. Examples of the available heating source include steam, electricity, UV light, IR light, and a heat medium.

In the preparation of the surface-crosslinked superabsorbent polymer of the present disclosure, the surface crosslinking modification may be achieved by treating the superabsorbent base resin with the water-soluble polyvalent cationic salt, and then with a mixture of the polycarbonic acid-based copolymer and the surface crosslinking agent (e.g., alkylene carbonate) (2-step), or by treating the superabsorbent base resin with a mixture of the water-soluble polyvalent cationic salt, the polycarbonic acid-based copolymer, and the surface crosslinking agent (1-step). The surface-crosslinked superabsorbent polymer, whether prepared in the 2-step process or the 1-step process, is found to still retain high processability.

The method may further comprise milling the surface-crosslinked superabsorbent polymer, and classifying the milled superabsorbent polymer by particle size into particles with sizes of less than 150 μm, from 150 μm to less than 300 μm, from 300 μm to less than 600 μm, from 600 μm to 850 μm, and greater than 850 μm. The milling step may be carried out with a mill the examples of which include, but are not limited to, a ball mill, a pin mill, a hammer mill, a screw mill, a roll mill, a disc mill, and a jog mill The surface-crosslinked superabsorbent polymer prepared according to the method of the present disclosure was observed to advance much in permeability and particularly to exhibit excellent permeability, compared to conventional SAPs, even though neither silica nor an organic solvent is employed.

With regard to other descriptions of the SAPs of the preparation method according to the present disclosure, reference may be made to the surface-crosslinked SAPs according to the present disclosure.

Mode for Invention

A better understanding of the present disclosure may be obtained through the following examples that are set forth to illustrate, but are not to be construed as limiting the present disclosure. While specific embodiments of and examples for the invention are described above for illustrative purposes, various equivalent modifications are possible within the scope of the invention, as those skilled in the relevant art will recognize. In addition, unless stated otherwise, the terms "%" and "part", as used in the context of amount, are on the basis of mass. Preparation of Hydrogel Phase Polymer and Superabsorbent Base Resin A monomer mixture was obtained by mixing 100 g of acrylic acid, 0.3 g of polyethylene glycol diacrylate as a crosslinking agent, 0.033 g of diphenyl(2,4,6-trimethylbenzoyl)-phosphine oxide as an initiator, 38.9 g of caustic soda (NaOH), and 103.9 g of water. The monomer mixture was fed onto a continuously moving conveyer belt, and subjected to polymerization for 2 min under UV light (intensity: 2 mW/cm$^2$) to obtain a hydrogel phase polymer. The hydrogel phase polymer obtained in Preparation Example 1 was cut into a size of 5×5 mm, dried for 2 hrs at 170° C. in a hot air dryer, milled using a pin mill, and screened with a sieve to give superabsorbent base resin particles with a size of 150 to 850 μm. Preparation of Polycarbonic Acid-Based Copolymer #427

To a 2-L glass reactor equipped with a thermometer, a stirrer, a dropping funnel, a nitrogen inlet, and a reflux condenser was added 200 parts by weight of water, and the reactor was purged with nitrogen gas and heated to 75° C. while the water was stirred.

After 20 parts by weight of an aqueous 3% by weight ammonium persulfate solution was added and slowly dissolved in the reactor, an aqueous monomer solution containing 400 parts by weight of methoxypolyethylene glycol monomethacrylate (average addition mole number of ethylene oxide of 100), 40 parts by weight of acrylic acid, 40 parts by weight of methacrylic acid, and 90 parts by weight of water, a mixture solution of 3.0 parts by weight of 2-mercapto ethanol and 30 parts by weight of water, and 70 parts by weight of an aqueous 3% by weight ammonium persulfate solution were dropwise added over 4 hrs. Thereafter, 10 parts by weight of an aqueous 3% by weight ammonium persulfate solution was added at once. Then, the solution was maintained at 75° C. for 1 hr.

After completion of the polymerization, the reaction mixture was cooled to room temperature, and neutralized for about 1 hr with an aqueous 30% by weight sodium hydroxide solution to afford a water-soluble copolymer salt with a solid content of 45%. The water-soluble copolymer salt was found to have a weight average molecular weight of 40,000 as measured by GPC (Gel Permeation Chromatography).

Preparation Example 1

In a high-speed mixer, 250 g of the superabsorbent base resin was mixed at 1000 rpm for 20 sec, and a previously prepared aqueous solution (0.5 g or 0.75 g of ethylene carbonate, 0.55 g of oxalic acid, 7.5 g of distilled water, and 8.75 g of methanol) was injected into the mixer through a plastic syringe, followed by mixing for an additional 3 min After the mixer was allowed to slowly stop by setting at 0 rpm, the resulting superabsorbent resin was as evenly spread as possible on a SUS tray, incubated for 40 min in an over preheated to 200° C., and then cooled at room temperature. The resin was screened with a sieve to give superabsorbent polymer particles with a size of 300 to 600 μm.

Preparation Example 2

In a high-speed mixer, 250 g of the superabsorbent base resin was mixed at 1000 rpm for 20 sec. Separately, 1.6545 g of polycarbonic acid-based copolymer #427 (LG Chem) was dissolved in 18.033 g of distilled water, followed by 1.5625 g of $Zr(SO_4)_2 \cdot 14\text{-}18H_2O$ (Junsei) and then ethylene carbonate. The resulting solution was injected into the mixer through a plastic syringe and mixed for an additional 3 min After the high-speed mixer was stopped by setting at 0 rpm, the resulting resin was as evenly spread as possible on a SUS tray, incubated for 40 min in an over preheated to 200° C., and then cooled at room temperature. The resin was screened with a sieve to give superabsorbent polymer particles with a size of 300 to 600 μm.

Preparation Example 3

In a high-speed mixer, 250 g of the superabsorbent base resin was mixed at 1000 rpm for 20 sec, and 6.25 g of an aqueous solution of $Zr(SO_4)_2 \cdot 14\text{-}18H_2O$ (Junsei) was injected into the mixer through a plastic syringe, followed by mixing for 3 min. Separately, 1.6545 g of polycarbonic acid-based copolymer #427 (LG Chem) was dissolved in 13.3455 g of distilled water, followed by ethylene carbonate. The resulting solution was injected into the mixer through a plastic syringe and mixed for an additional 3 min After the high-speed mixer was stopped by setting at 0 rpm, the resulting resin was as evenly spread as possible on a SUS tray, incubated for 40 min in an over preheated to 200° C., and then cooled at room temperature. The resin was screened with a sieve to give superabsorbent polymer particles with a size of 300 to 600 μm.

Preparation Example 4

In a ball mill, 20.0 g of each of the superabsorbent polymers prepared in Preparation in Examples 1 to 3 was milled for 20 min with 10 ceramic balls. The milled polymer was screened with a standard sieve to give superabsorbent polymer particles with a size of 300 to 600 μm.

Examples 1 to 8 and Comarative Examples 1 to 4:
Preparation of Surface-Crosslinked SAPs Under the conditions listed in Table 3, below, SAPs of Examples 1 to 8 and Comparative Examples 1 to 4 were prepared.

TABLE 3

427 Polymer with Surface Crosslinked with $Zr(SO_4)_2$ and Ethylene Carbonate (EC)

| Ex. # | Ball Mill | # of Steps | Preparation | $Zr(SO_4)_2 \cdot 14\text{-}18H_2O$ Amount (g) | $H_2O$ (g) | #427 Amount (g) | $H_2O$ (g) | Reagent EG (g) | Others (g) |
|---|---|---|---|---|---|---|---|---|---|
| C. 1 | Before | Control | Prep. Ex. 1 | — | — | — | — | 0.5 | Oxailic acid 0.55 |
| C. 2 | After | | Prep. Ex. 1&4 | | | | | | Methanol 8.75 |
| C. 3 | Before | | Prep. Ex. 1 | | | | | 0.75 | Distilled water 7.5 |
| C. 4 | After | | Prep. Ex. 1&4 | | | | | | |
| 1 | Before | 1-Step | Prep. Ex. 2 | 1.5625 | 4.6875 | 1.6545 | 13.3455 | 0.5 | — |
| 2 | After | | Prep. Ex. 2&4 | | | | | | |
| 3 | Before | | Prep. Ex. 2 | | | | | 0.75 | |
| 4 | After | | Prep. Ex. 2&4 | | | | | | |
| 5 | Before | 2-Step | Prep. Ex. 3 | | | | | 0.5 | |
| 6 | After | | Prep. Ex. 3&4 | | | | | | |
| 7 | Before | | Prep. Ex. 3 | | | | | 0.75 | |
| 8 | After | | Prep. Ex. 3&4 | | | | | | |

TABLE 4

| | | | | Physical Properties | | | | |
|---|---|---|---|---|---|---|---|---|
| | CRC | AUP | Permeability | Particle Size Distribution (PSD, %) | | | | |
| Ex. # | (g/g) | (g/g) | (sec) | >850 μm | 600-850 μm | 300-600 μm | 150-300 μm | <150 μm |
| C. 1 | 30.1 | 22.5 | 123 | 2.25 | 50.94 | 40.24 | 6.10 | 0.46 |
| C. 2 | 32.2 | 20.7 | 371 | 0.00 | 0.05 | 67.37 | 25.71 | 6.87 |
| C. 3 | 29.8 | 21.4 | 148 | 0.85 | 46.94 | 43.38 | 8.09 | 0.74 |
| C. 4 | 32.0 | 19.2 | 412 | 0.00 | 0.05 | 66.92 | 25.54 | 7.49 |
| 1 | 31.8 | 22.7 | 120 | 0.08 | 41.53 | 45.45 | 10.58 | 2.36 |
| 2 | 33.7 | 20.1 | 430 | 0.00 | 0.11 | 83.06 | 13.10 | 3.73 |
| 3 | 27.6 | 21.8 | 23 | 0.13 | 40.37 | 44.43 | 12.46 | 2.62 |
| 4 | 28.8 | 21.4 | 60 | 0.00 | 0.15 | 81.29 | 13.69 | 4.87 |
| 5 | 28.2 | 23.0 | 41 | 0.12 | 37.43 | 49.82 | 11.52 | 1.10 |
| 6 | 30.7 | 22.1 | 85 | 0.00 | 0.15 | 71.17 | 21.78 | 6.90 |
| 7 | 29.8 | 23.0 | 58 | 0.28 | 39.40 | 47.67 | 11.45 | 1.20 |
| 8 | 32.6 | 19.6 | 156 | 0.00 | 0.10 | 72.03 | 20.62 | 7.24 |

Figure 1A:
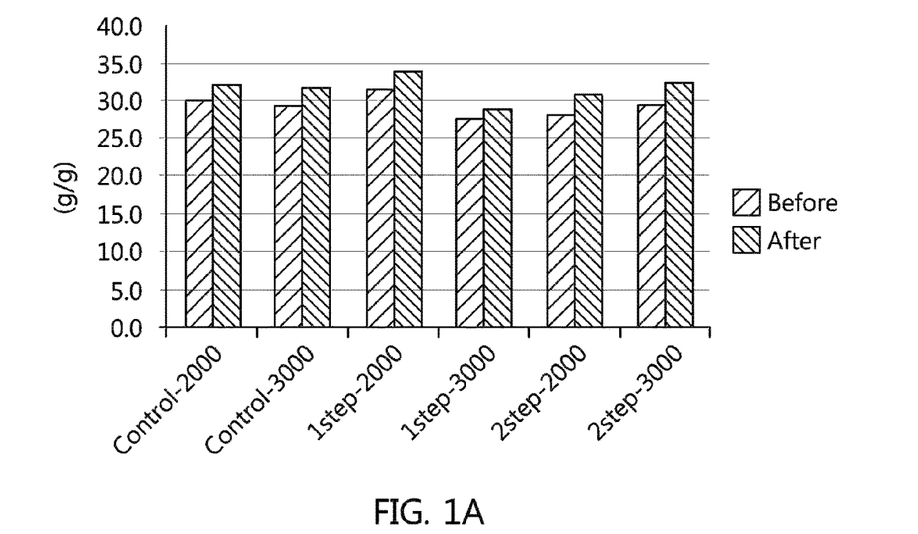
FIG. 1a is a graph showing CRC changes in SAPs between pre- and post-ball milling (Comparative Example 1, Comparative Example 2, Comparative Example 3, Comparative Example 4, Example 1, Example 2, Example 3, Example 4, Example 5, Example 6, Example 7, and Example 8 from the left to the right).
Figure 1B:
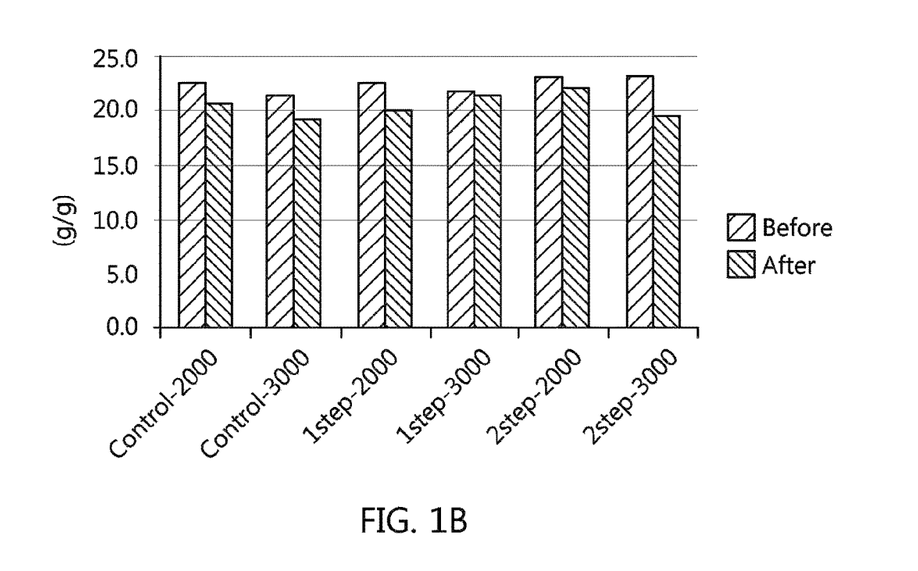
FIG. 1b is a graph showing AUP changes in SAPs between pre- and post-ball milling (Comparative Example 1, Comparative Example 2, Comparative Example 3, Comparative Example 4, Example 1, Example 2, Example 3, Example 4, Example 5, Example 6, Example 7, and Example 8 from the left to the right).
Figure 1C:
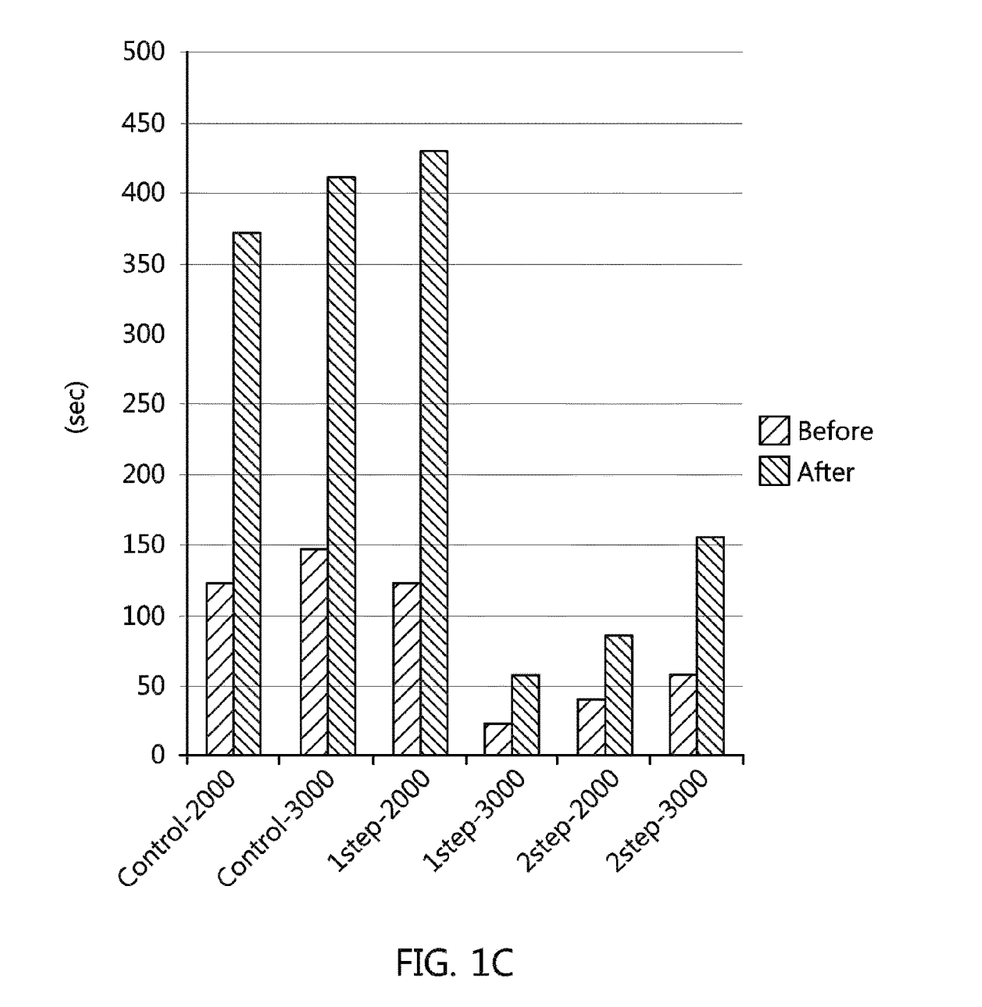
FIG. 1c is a graph showing permeability changes in SAPs between pre- and post-ball milling (Comparative Example 1, Comparative Example 2, Comparative Example 3, Comparative Example 4, Example 1, Example 2, Example 3, Example 4, Example 5, Example 6, Example 7, and Example 8 from the left to the right).
Figure 2A:
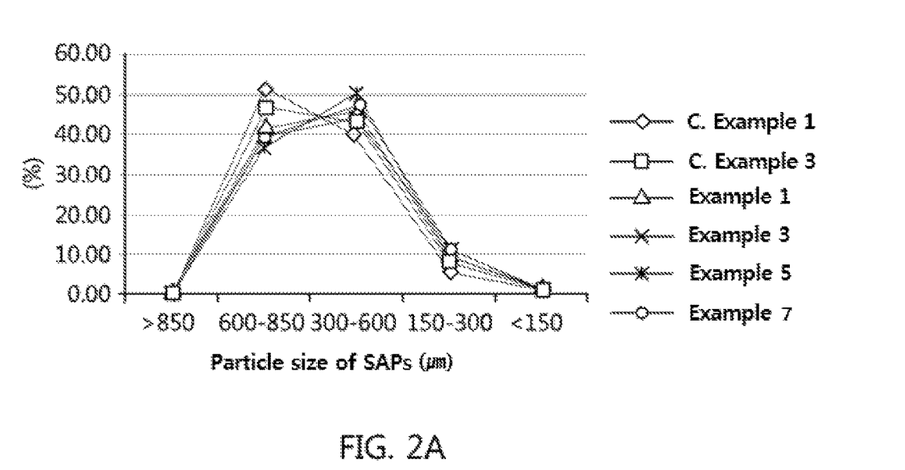
FIG. 2a is a graph showing particle size distributions of SAPs before ball milling.
Figure 2B:
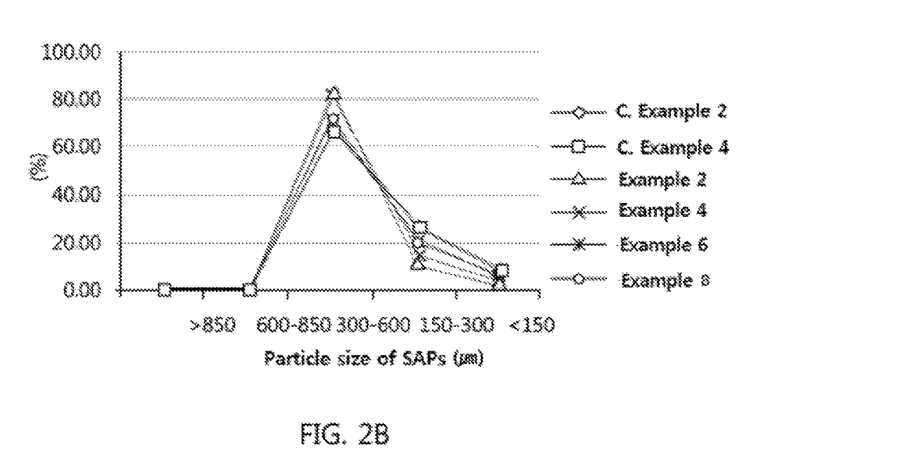
FIG. 2b is a graph showing particle size distributions of SAPs after ball milling.

For reference, in FIGS. 1a to 1c wherein the data of Table 4 are depicted, the variables on the x-axis control-2000, control-3000, 1 step-2000, 1 step-3000, 2 step-2000, and 2 step-3000 correspond respectively to Comparative Examples 1 and 2, Comparative Examples 3 and 4, Examples 1 and 2, Examples 3 and 4, Examples 5 and 6, and Examples 7 and 8.

Test Examples: Assay for Physical Properties

Test Example 1: Particle Size Distribution

The SAPs prepared in Preparation Examples 1 to 4 were measured for particle size distribution. The measurement was conducted according to the EDANA-recommended method WSP 240.3. For this, the SAP particles prepared in Examples 1 to 8 and Comparative Examples 1 to 4 were placed in an amount of 100 g on each of 850 μm, 600 μm, 300 μm, and 150 μm pan meshes, and vibrated for 10 min with an amplitude of 1.00 mm. The amount of the particles held up on each sieve was measured to calculate the content as a percentage.

Test Example 2: Centrifugal Retention Capacity (CRC)

Each of the SAPs prepared in Preparation Examples 1 to 4 was measured for centrifugal retention capacity (CRC). The measurement of CRC was carried out according the EDANA (European Disposables and Nonwovens Association)-recommended method WSP 241.3(10) (IST 241.2(02). W grams (about 0.1 g) of each of the SAPs with a particle size of 300 to 600 μm, prepared in Examples 1 to 8 and Comparative Examples 1 to 4, was placed in a non-woven bag that was then sealed, and immersed into 0.9 mass % saline. After 30 min of immersion, centrifugation was carried out at 250×g for 3 min for dewatering. The dewatered bag alone weighed W2 (g). The same procedure was repeated, with the exception that no resins were employed. In this regard, the dewatered bag alone weighed W1 (g). CRC (g/g) was calculated from the weight measurements according to the following equation.

$$CRC(g/g)=\{(W2(g)-W1(g))/W(g)\}-1 \qquad \text{[Math Equation 1]}$$

Test Example 3: Absorption Under Pressure (AUP)

Each of the SAPs prepared in Preparation Examples 1 to 4 was measured for absorption under pressure (AUP). The measurement of AUP was carried out according the EDANA (European Disposables and Nonwovens Association)-recommended method WSP 242.3 (11) (IST 242.2(02)). Briefly, a stainless-steel 400 mesh net was welded onto the bottom of a plastic supporting cylinder having an internal diameter of 60 mm. Then, 0.90 g of each of the SAPs with a particle size of 300 to 600 μm, prepared in Examples 1 to 8 and Comparative Examples 1 to 4, was evenly sprayed onto that metal net on the bottom at room temperature and a RH of 50%. A piston was placed so as to evenly impart a load of 4.83 kPa (0.7 psi) to the sprayed resin. The piston had an external diameter slightly less than 60 mm such that it smoothly moved vertically within the cylinder, with no spaces left between the external wall of the piston and the internal wall of the cylinder. The resulting cylinder weighed Wa (g).

A 5-mm thick glass filter with a diameter of 90 mm was placed in a 150-mm petri dish. A physiological saline containing 0.90% by weight of sodium chloride was added until it was flush with the top side of the glass filter. A sheet of filter paper with a diameter of 90 mm was placed on the saline. Then, a measuring device set was placed on the wet filter paper so that the paper could absorb the solution under the load. An hour later, the measuring device set was lifted, and the resulting cylinder weighed Wb (g).

Absorbency under pressure was calculated from the measurements Wa and Wb according to the following equation:

$$AUP(g/g)=[Wb(g)-Wa(g)]/\text{Wt. of absorbent resin}(g) \qquad \text{[Math Equation 2]}$$

Test Example 4: Permeability

Each of the SAPs prepared in Preparation Examples 1 to 4 was measured for permeability. Briefly, 0.2 g of each of the SAPs with a particle size of 300 to 600 μm, prepared in Examples 1 to 8 and Comparative Examples 1 to 4, was placed in a 20-mm diameter cylinder installed on the bottom with a glass filter and a stopcock, and 50 g of 0.9% saline was poured along the wall so that the SAPs were washed down. After 30 min, the SAPs were pressed for 1 min using a piston loaded with a balance (a total of 0.3 psi) before the stopcock was opened. Permeability was determined by measuring the time taken for the surface of the saline to reach the marked arrival line (the surface level of 20 ml saline in the cylinder under the piston) from the marked start line (the surface level of 40 ml saline in the cylinder under the piston) using a stopwatch.

The SAPs having the surface of which was treated with a mixture of the water-soluble polyvalent cationic salt and the polycarbonic acid-based copolymer in accordance with the present disclosure were greatly improved in permeability even though neither silica nor an organic solvent is used for the base resin, resulting in an effective reduction in process time and cost. In addition, as is understood from data of Table 4, the SAPs of the present disclosure were found, particularly after ball milling, to increase in particle size distribution from 300 μm to less than 600 μm and to decrease in particle size distribution from 150 μm to less than 300 μm. With an increase in the particle size distribution from 300 μm to less than 600 μm, the SAPs were more homogeneously mixed with the surface crosslinking agent to improve both the absorption properties (CRC, AUP) and permeability, which resulted in excellent processability, compared to conventional SAPs. The permeability is deeply associated with the breakdown of the resin. The SAPs of Comparative Example 1 in which neither water-soluble polyvalent ions nor a polycarbonic acid-based copolymer were employed became poor in permeability after ball milling (Comparative Example 2). In contrast, the SAPs of the present disclosure were unlikely to change in permeability even after ball milling, indicating that the SAPs of the present disclosure are likely to retain physical properties even under external pressures and impacts such as physical breakdown. Taken together, the data obtained above demonstrate that the surface crosslinking modification according to the present disclosure ensures not only excellent permeability but also other properties.

The invention claimed is:

1. A surface-crosslinked superabsorbent polymer, wherein a base resin of a superabsorbent polymer is surface cross-linked with a water-soluble polyvalent cationic salt, a polycarbonic acid-based copolymer, and a surface crosslinking agent.

2. The surface-crosslinked superabsorbent polymer of claim 1, wherein the water-soluble polyvalent cationic salt is contained in an amount of 0.001 to 5.0 parts by weight, based on 100 parts by weight of the superabsorbent base resin.

3. The surface-crosslinked superabsorbent polymer of claim 1, wherein the water-soluble polyvalent cationic salt comprise a cationic ion selected from the group consisting of $Al^{3+}$, $Zr^{4+}$, $Sc^{3+}$, $Ti^{4+}$, $V^{5+}$, $CR^{3+}$, $Mn^{2+}$, $Fe^{3+}$, $Ni^{2+}$, $Cu^{2+}$, $Zn^{2+}$, $Ag^+$, $Pt^{4+}$, $Au^+$, and a combination thereof, and an anion selected from the group consisting of sulfate ($SO_4^{2-}$), sulfite ($SO_3^{2-}$), nitrate ($NO^{3-}$), metaphosphate ($PO^{3-}$), phosphate ($PO_4^{3-}$), and a combination thereof.

4. The surface-crosslinked superabsorbent polymer of claim 3, wherein water-soluble polyvalent cationic salt is aluminum sulfate ($Zr(SO_4)_2$) or zirconium sulfate ($Zr(SO_4)_2$).

5. The surface-crosslinked superabsorbent polymer of claim 1, wherein the polycarbonic acid-based copolymer is contained in an amount of 0.001 to 5.0 parts by weight, based on 100 parts by weight of the superabsorbent polymer.

6. The surface-crosslinked superabsorbent polymer of claim 1, wherein the polycarbonic acid-based copolymer contains an alkoxypolyalkylene glycol mono(meth)acrylic acid ester monomer and a (meth)acrylic acid monomer.

7. The surface-crosslinked superabsorbent polymer of claim 6, wherein the alkoxypolyalkylene glycol mono(meth)acrylic acid ester monomer is represented by the following Chemical Formula 1:

wherein, $R^1$ is a hydrogen atom or methyl;

$R^2O$ represents an oxyalkylene moiety of 2 to 4 carbon atoms;

$R^3$ is alkyl of 1 to 4 carbon atoms; and m is an integer of 50 to 200, expressing an average addition mole number of oxyalkylene.

8. The surface-crosslinked superabsorbent polymer of claim 6, wherein the alkoxypolyalkylene glycol mono(meth)acrylic acid ester monomer is at least one selected from the group consisting of methoxypolyethylene glycol mono(meth)acrylate, methoxypolypropylene glycol mono(meth)acrylate, methoxypolybutylene glycol mono(meth)acrylate, methoxypolyethylene glycol polypropylene glycol mono(meth)acrylate, methoxypolyethylene glycol polybutylene glycol mono(meth)acrylate, methoxypolypropylene glycol polybutylene glycol mono(meth)acrylate, methoxypolyethylene glycol polypropylene glycol polybutylene glycol mono(meth)acrylate, ethoxypolyethylene glycol mono(meth)acrylate, ethoxypolypropylene glycol mono(meth)acrylate, ethoxypolybutylene glycol mono(meth)acrylate, ethoxypolyethylene glycol polypropylene glycol mono(meth)acrylate, ethoxypolyethylene glycol polybutylene glycol mono(meth)acrylate, ethoxypolypropylene glycol polybutylene glycol mono(meth)acrylate, and ethoxypolyethylene glycol polypropylene glycol polybutylene glycol mono(meth)acrylate.

9. The surface-crosslinked superabsorbent polymer of claim 6, wherein the (meth)acrylic acid monomer is represented by the following Chemical Formula 2:

[Chemical Formula 2]

wherein, $R^2$ is an unsaturated hydrocarbon of 2 to 5 carbon atoms; and $M^1$ is a hydrogen atom, a monovalent or divalent metal, an ammonium group, or an organic amine group.

10. The surface-crosslinked superabsorbent polymer of claim 1, wherein the (meth)acrylic acid monomer is at least one selected from the group consisting of an acrylic acid, a methacrylic acid, a monovalent or divalent metal salt thereof, an ammonium salt thereof, and an organic amine salt thereof.

11. The surface-crosslinked superabsorbent polymer of claim 1, wherein the surface crosslinking agent is contained in an amount of 0.001 to 5.0 parts by weight, based on 100 parts by weight of the superabsorbent base resin.

12. The surface-crosslinked superabsorbent polymer of claim 1, wherein the surface crosslinking agent is selected from the group consisting of a polyhydric compound; an epoxy compound; a polyamine compound; a haloepoxy compound; a haloepoxy compound condensate; an oxazoline compound; a mono-, di- or polyoxazolidinone compound; a cyclic urea compound; an alkylene carbonate compound; and a combination thereof.

13. A method for preparing a surface-crosslinked superabsorbent polymer, comprising:

a) providing a superabsorbent base resin;

b) pre-treating the superabsorbent base resin of step a) by mixing a water-soluble polyvalent cationic salt in an amount of 0.001 to 5.0 parts by weight, based on 100 parts by weight of the superabsorbent base resin provided in step a); and c) subjecting the pre-treated superabsorbent base resin of step b) to surface crosslinking modification with a mixture solution comprising a polycarbonic acid-based copolymer in an amount of 0.001 to 5.0 parts by weight and a surface crosslinking agent in an amount of 0.001 to 5.0 parts by weight, based on, based on 100 parts by weight of the superabsorbent base resin.

14. A method for preparing a surface-modified superabsorbent polymer, comprising:

a) providing a superabsorbent base resin;

b) preparing a mixture solution comprising a water-soluble polyvalent cationic salt in an amount of 0.001 to 5.0 parts by weight, a polycarbonic acid-based copolymer in an amount of 0.001 to 5.0 parts by weight, and a surface crosslinking agent in an amount of 0.001 to 5.0 parts by weight, based on 100 parts by weight of the superabsorbent base resin; and c) subjecting the superabsorbent bas resin of step a) to surface crosslinking modification with the mixture solution of step b).

15. The method of claim 13, wherein the surface crosslinking modification is carried out at 100 to 300° C. for 1 to 90 min.

16. The method of claim 13 or 14, wherein the water-soluble polyvalent cationic salt comprise a cationic ion selected from the group consisting of $Al^{3+}$, $Zr^{4+}$, $Sc^{3+}$, $Ti^{4+}$, $V^{5+}$, $CR^{3+}$, $Mn^{2+}$, $Fe^{3+}$, $Ni^{2+}$, $Cu^{2+}$, $Zn^{2+}$, $Ag^+$, $Pt^{4+}$, $Au^+$, and a combination thereof, and an anion selected from the group consisting of sulfate ($SO_4^{2-}$), sulfite ($SO_3^{2-}$), nitrate ($NO^{3-}$), metaphosphate ($PO^{3-}$), phosphate ($PO_4^{3-}$), and a combination thereof.

17. The method of claim 16, wherein the water-soluble polyvalent cationic salt is aluminum sulfate ($Zr(SO_4)_2$) or zirconium sulfate ($Zr(SO_4)_2$).

18. The method of claim 13 or 14, wherein the polycarbonic acid-based copolymer contains an alkoxypolyalkylene glycol mono(meth)acrylic acid ester monomer and a (meth) acrylic acid monomer.

19. The method of claim 14, wherein the surface crosslinking modification is carried out at 100 to 300° C. for 1 to 90 min.

20. The method of claim 14, wherein the water-soluble polyvalent cationic salt comprise a cationic ion selected from the group consisting of $Al^{3+}$, $Zr^{4+}$, $Sc^{3+}$, $Ti^{4+}$, $V^{5+}$, $CR^{3+}$, $Mn^{2+}$, $Fe^{3+}$, $Ni^{2+}$, $Cu^{2+}$, $Zn^{2+}$, $Ag^+$, $Pt^{4+}$, $Au^+$, and a combination thereof, and an anion selected from the group consisting of sulfate ($SO_4^{2-}$), sulfite ($SO_3^{2-}$), nitrate ($NO^{3-}$), metaphosphate ($PO^{3-}$), phosphate ($PO_4^{3-}$), and a combination thereof.

21. The method of claim 20, wherein the water-soluble polyvalent cationic salt is aluminum sulfate ($Zr(SO_4)_2$) or zirconium sulfate ($Zr(SO_4)_2$).

22. The method of claim 14, wherein the polycarbonic acid-based copolymer contains an alkoxypolyalkylene glycol mono(meth)acrylic acid ester monomer and a (meth) acrylic acid monomer.

* * * * *